US008653965B1

(12) United States Patent
Otto et al.

(10) Patent No.: US 8,653,965 B1
(45) Date of Patent: Feb. 18, 2014

(54) HUMAN HEALTH MONITORING SYSTEMS AND METHODS

(75) Inventors: Chris A. Otto, Huntsville, AL (US); Chirag D. Patel, Chicago, IL (US); Hugh A. Hartwig, Madison, AL (US); Corey L. Sanders, Madison, AL (US)

(73) Assignee: Integrity Tracking, LLC, Boca Raton, FL (US)

( * ) Notice: Subject to any disclaimer, the term of this patent is extended or adjusted under 35 U.S.C. 154(b) by 980 days.

(21) Appl. No.: 12/686,342

(22) Filed: Jan. 12, 2010

Related U.S. Application Data

(60) Provisional application No. 61/144,068, filed on Jan. 12, 2009, provisional application No. 61/144,050, filed on Jan. 12, 2009.

(51) Int. Cl.
*G08B 1/08* (2006.01)

(52) U.S. Cl.
USPC ............. 340/539.12; 340/539.11; 340/573.1; 340/539.22; 340/286.01; 340/286.07; 370/401; 370/390

(58) Field of Classification Search
USPC ............... 340/539.11, 539.12, 573.1, 539.22, 340/286.01, 539.17, 286.07; 600/300; 705/2, 3, 5; 370/401, 390
See application file for complete search history.

(56) References Cited

U.S. PATENT DOCUMENTS

| | | | |
|---|---|---|---|
| 2005/0190055 A1* | 9/2005 | Petite ............................ 340/531 |
| 2005/0206518 A1* | 9/2005 | Welch et al. ............. 340/539.12 |
| 2005/0275541 A1* | 12/2005 | Sengupta et al. .......... 340/573.1 |
| 2007/0069887 A1* | 3/2007 | Welch et al. ............. 340/539.12 |
| 2007/0164857 A1* | 7/2007 | Odenwald et al. ....... 340/539.22 |
| 2007/0273504 A1* | 11/2007 | Tran ......................... 340/539.12 |
| 2008/0001735 A1* | 1/2008 | Tran ......................... 340/539.22 |
| 2008/0004904 A1* | 1/2008 | Tran ................................ 705/2 |
| 2008/0211657 A1* | 9/2008 | Otto ............................ 340/501 |
| 2008/0211665 A1* | 9/2008 | Mazar et al. ............. 340/539.17 |
| 2008/0246629 A1* | 10/2008 | Tsui et al. ................ 340/870.07 |
| 2008/0309481 A1* | 12/2008 | Tanaka et al. ............ 340/539.12 |
| 2009/0058635 A1* | 3/2009 | LaLonde et al. ......... 340/539.11 |
| 2009/0058636 A1* | 3/2009 | Gaskill et al. ............ 340/539.11 |
| 2009/0062887 A1* | 3/2009 | Mass et al. ...................... 607/60 |
| 2009/0063193 A1* | 3/2009 | Barton et al. .................... 705/3 |
| 2009/0146822 A1* | 6/2009 | Soliman ..................... 340/573.1 |

* cited by examiner

*Primary Examiner* — Hoi Lau
(74) *Attorney, Agent, or Firm* — Ann I. Dennen; Lanier Ford Shaver & Payne P.C.

(57) ABSTRACT

A monitoring system of the present disclosure has at least one monitor that collects personal health data, stores the personal health data in memory, and transmits at least one data packet comprising the personal health data and at least one identifier for identifying the monitor and a gateway computing device communicatively coupled to the at least one monitor and communicatively coupled to a network, the gateway computing device receives from the monitor the at least one data packet and transmits the at least one data packet over the network. In addition, the monitoring system has a server computing device communicatively coupled to the network, the server computing device receives from the gateway computing device the data packet and stores the data packet in memory associated with a user identifier.

56 Claims, 7 Drawing Sheets

HUMAN HEALTH MONITORING SYSTEMS AND METHODS

CROSS REFERENCE TO RELATED APPLICATIONS

This application claims priority to U.S. Provisional Patent Application Ser. No. 61/144,068, entitled "Digital System for Remote Human Health Monitoring and Emergency Alert," and filed on Jan. 12, 2009, and U.S. Provisional Patent Application Ser. No. 61/144,050, entitled "Application Server and Graphical User Interface for Real Time Health Monitoring," and filed on Jan. 12, 2009, each of which is incorporated herein by reference.

BACKGROUND

Health monitoring devices are known and used in various fields, including medical instrumentation, personal health monitoring, wireless sensor networks, and computing. Such devices are used for monitoring, recording, and reporting physiological signals. For example, health monitoring devices typically include self-test devices such as weight scales for monitoring a user's weight; blood pressure cuffs for monitoring blood pressure; heart rate monitor for monitoring heart rate; temperature sensors for monitoring skin (or core body) temperature; and Personal Emergency Response System (PERS) devices. Data is typically either retrieved and analyzed as a post recording session or acquired in real-time continuously from the device.

Emergency Alert Systems are known in the field of personal emergency response systems (PERS) and in the field of home security. Emergency alert systems allow individuals to signal for help.

The collection of visualization of data collected from these devices is typically partitioned into 3 components: the device; a network access device or gateway; and an application server. The device typically communicates with the gateway or controller with either a wired or wireless interface such as Zigbee, WiFi, or Ethernet. The data is collected by the network access device or gateway and uploaded to an application server which stores the data and commonly provides a user interface to visualize and report the data.

SUMMARY

A monitoring system in accordance with an embodiment of the present disclosure has at least one monitor that collects personal health data, stores the personal health data in memory, and transmits at least one data packet comprising the personal health data and at least one identifier for identifying the monitor. In addition, the monitoring system has a gateway computing device communicatively coupled to one or more monitors, the gateway computing device receives from the monitor at least one data packet and transmits at least one data packet over a network. Furthermore, the monitoring system has a server computing device communicatively coupled to the network, the server computing device receives from the gateway computing device the data packet and stores the data packet in memory associated with a user identifier.

A monitoring method in accordance with an embodiment of the present disclosure comprises receiving a data packet from a monitor, the data packet comprising at least one unique identifier and personal health data, storing data indicative of the data packet on a gateway computing device, and repackaging the data packet. The monitoring method further comprises transmitting the repackaged data packet to a server computing device, the repackaged data comprising at least one unique identifier and personal health data, receiving the repackaged data packet, and storing data indicative of the personal health data in memory correlated with the unique identifier.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

A monitoring system in accordance with an exemplary embodiment of the present disclosure periodically monitors health metrics of a user in the user's natural setting. The system provides early detection of abnormal physiological levels and builds a history of the user's health information. For example, the monitoring system measures the user's activity (Activity-induced Energy Expenditure), heart rate, skin temperature, number of steps taken, and his/her sleep/wake patterns.

The monitoring system is capable of monitoring a user remotely and includes at least one wearable monitor, a gateway computing device, a server computing device for storing user health information, and a data receiving device that allows third parties to monitor the health and other information of the user of the system.

The monitoring system comprises of any number of measurement devices including body worn health monitoring devices, such as chest straps, wrist watches, pendants, or patches; self-test devices such as weight scales, blood pressure cuffs, glucose meters, peak flow meter, and pulse oximeter sensors; an application specific network access device herein referred as the home gateway; an application server enabling remote management of the user being monitored; and a number of methods for contacting caregivers and system users in the event of an emergency or non-emergency alert.

The monitoring system simplifies both user experience and the caregiver experience by converging health, wellness, and emergency response. The user is instrumented with the monitor in a way that is comfortable and substantially non-intrusive, or uses passive and/or active sensors. Some devices are capable of detecting emergency conditions such as a user-initiated alert (e.g. pressing a panic button) while others may be intelligent and capable of automatically detecting an alert such as a user falling—especially desirable in the case of a senior user or a user with disabilities. Other automatic devices may include devices in the user's environment such as door switches or sensors to detect extreme climate changes or sensors to detect that an appliance was left on for an extended period of time—all especially of interest to elderly users.

The monitoring system allows remote monitoring of a user via the Internet, via cellular telephones, and/or to engage caregivers to take action in the event of an emergency.

In addition, the monitoring system collects and archives all historical health information on behalf of a user, organizes the information into a relational database, and shares the information with caregivers.

Figure 1:
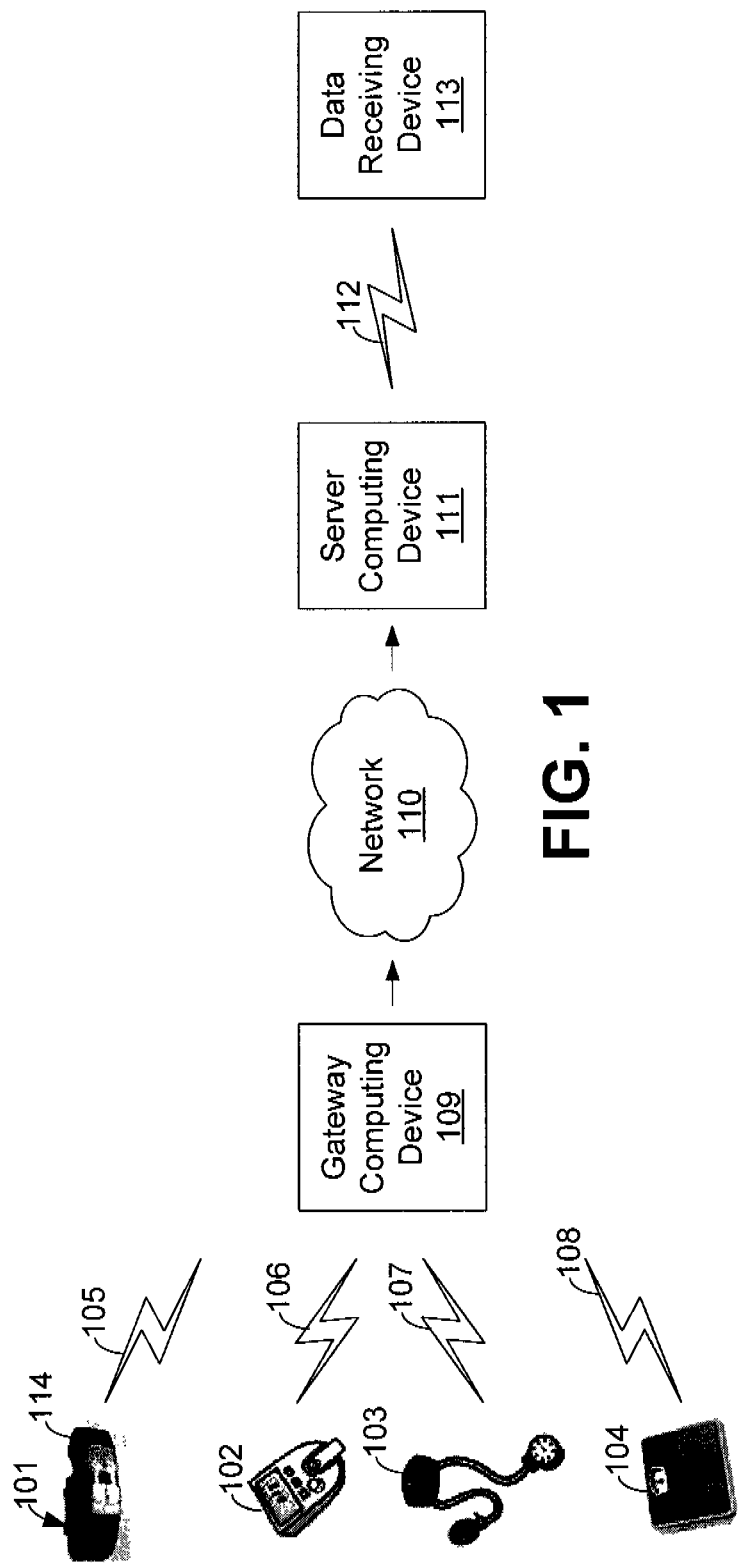
FIG. 1 is a block diagram depicting a monitoring system in accordance with an embodiment of the present disclosure.

FIG. 1 is a block diagram of an exemplary monitoring system 100 in accordance with an embodiment of the present disclosure. The system 100 comprises one or more monitors 101-104 that are communicatively coupled to a gateway computing device 109 via one or more communication links 105-108, respectively. Notably, any of the monitors 101-104 may further share a communication link, as well, with any of the other monitors 101-104.

In this regard, the monitors 101-104 include a wearable device monitor 101, a glucose monitor 102, a blood pressure monitor 103, and a weight monitor 104. Note that such monitoring devices 101-104 are shown for exemplary purposes and other types of monitoring devices may be used in other embodiments of the monitoring system 100.

In one embodiment, the communication links 105-108 are wireless communication links, which can be infrared (IR) or radio-frequency (RF) links capable of transferring information from the monitoring devices 101-104 to the gateway computing device 109. Various wireless communication interfaces and data transfer protocols support the communication of information from the monitoring devices 101-104 and the gateway computing device 109. By way of example, infrared data association (IrDA) protocols, ZigBee®, IEEE 802.15.4, BlueTooth®, IEEE 802.15.1, or IEEE 802.11 Wi-Fi are exemplary protocols that support wireless data transfers. In addition, any of the monitors 101-104 may also be physically coupled to the gateway computing device 109 such that wireless communication is unnecessary. For example, the monitors 101-104 may be physically coupled to the gateway computing device via Universal Serial Bus (USB), Firewire, Ethernet, or RS-232.

In one embodiment, the wearable device monitor 101 comprises a strap 114 that is worn about a user's body area (not shown). The wearable device monitor 101 monitors both health status and physiological signals. In addition, in the case of emergency response functions, the wearable device monitor 101 transmits data indicative of an emergency, e.g., a fall. Note that a the wearable device monitor 101 may be worn about or otherwise coupled to body areas, such as the user's chest, waist, wrist, or upper arm, or optionally a harness device as opposed to the wearable device monitor 101 that is worn about the user's chest. In this regard, the wearable device monitor 101 may be a belt clip that is worn on the user's belt or an upper arm band that is worn around the user's upper arm.

In one embodiment, the wearable device monitor 101 measures, stores, and transmits physiological information via the communication link 105 to the gateway computing device 109. In this regard, the wearable device monitor 101 communicates with the gateway computing device 109 via a messaging protocol that adequately describes pertinent health features, alert conditions, and wearable device monitor status information.

Non-limiting examples of physiological information that may be measured, stored and transmitted by the wearable device monitor 101 include heart rate, respiration, muscle activity, skin temperature; oxygen saturation sensors (SpO2); and galvanic skin response (GSR) sensors. Other non-limiting examples include motion data, data indicative of caloric expenditure or energy expenditure, number of steps, and data indicative of sleep/wake patterns.

In one embodiment, where seniors or disabled individuals may be wearing the wearable device monitor 101, a specific concern for detection of a fall or notification of other emergency alerts is of particular concern. In such an embodiment, the wearable device monitor 101 may have the capability to automatically detect a fall, which is described in U.S. patent application Ser. No. 12/192,855 entitled "Wearable Health Monitoring Device and Methods for Fall Detection" and filed on Aug. 15, 2008 and U.S. patent application Ser. No. 12/192,830 entitled "Wearable Health Monitoring Device and Methods for Step Detection" and filed on Aug. 15, 2008, which are incorporated herein by reference. In addition, the wearable device monitor 101 may automatically detect heart irregularities or other health anomalies. Furthermore, the wearable device monitor 101 may comprise a button (not shown) that the user may press as a signal for help.

In one embodiment, the wearable device monitor 101 may have a limited range of wireless communication with the gateway computing device 109. In such an embodiment, the wearable device monitor 101 may comprise a wide area network wireless access device (not shown). Thus, the wearable device monitor 101 may, at times, be able to communicate directly with the server computing device 111 when not within range with the gateway computing device 109. In this regard, the wearable device monitor 101 may comprise a baseband radio frequency (RF) transceiver (e.g., global system for mobile communications (GSM), code division multiple access (CDMA), general packet radio service (GPRS), Mobile WiMax or other mobile telecommunication standard) to communicate directly with the server computing device 111. Additionally, the wearable device monitor 101 may communicate with a cell phone, which in turn communicates with the server computing device 111.

In one embodiment, the glucose monitor 102 comprises a test strip port (not shown) that receives a test strip (not shown) on which a user's blood has been deposited. The glucose monitor 102 obtains from the user's blood data indicative of the glucose contained in the user's blood.

In one embodiment, the glucose monitor 102 measures, stores, and transmits data indicative of the glucose content information via the communication link 106 to the gateway computing device 109. In this regard, the glucose monitor 102 communicates with the gateway computing device 109 via a messaging protocol that adequately describes glucose content of the user's blood.

In one embodiment, the blood pressure monitor 103 comprises an inflatable cuff (not shown) that is placed around the user's arm (not shown). The inflatable cuff is inflated via an inflation bulb and valve (not shown), and the user's blood pressure is obtained via a device that is used to measure the pressure in the user's arm as the cuff is deflated. Thus, the blood pressure monitor 103 may obtain data indicative of the user's blood pressure and pulse.

In one embodiment, the blood pressure monitor 103 measures, stores, and transmits blood pressure and pulse information via the communication link 107 to the gateway computing device 109. In this regard, the blood pressure monitor 103 communicates with the gateway computing device 109 via a messaging protocol that adequately describes the user's blood pressure and pulse.

In one embodiment, the weight monitor 104 comprises weight scales (not shown). A user stands on the weight scales, and the weight monitor 104 obtains the weight of the user. In this regard, the weight monitor 104 obtains and stores data indicative of the user's weight.

In one embodiment, the weight monitor 104 measures, stores, and transmits weight information via the communication link 108 to the gateway computing device 109. In this regard, the weight monitor 104 communicates with the gateway computing device 109 via a messaging protocol that adequately describes the user's weight.

Note that as described above the monitors 101-104 collect data indicative of various health related characteristics of a user. Such data is hereinafter referred to as personal health data.

The monitoring system 100 further comprises a server computing device 111. The server computing device 111 is communicatively coupled to the gateway computing device 109 via a network 110. For example, in one embodiment, the network 110 is the Internet and Internet protocol (IP) packets are communicated between the gateway computing device 109 and the server computing device 111.

In addition, the monitoring system 100 further comprises a data receiving device 113 for receiving data from the server computing device 111. In this regard, the server computing device 111 communicates with the data receiving device 113 via a communication link 112.

The data receiving device 113 may be any type of device for receiving data from the server computing device 111. As mere examples, the data receiving device 113 may be a telephone, a monitoring call center, a personal digital assistant (PDA), a cell phone, or another computing device. To such types of devices, the server computing device 111 may transmit data, for example, of an alert indicating a critical situation with the user, e.g., the user has fallen.

In the example where the data receiving device 113 is a telephone, the server computing device 111 would receive alert condition. Upon receipt, the server computing device 111 would translate the data to audio speech. For example, the server computing device 111 may translate the data into a .wav file or any other sound file format known in the art or future-developed. In such an embodiment, the server computing device 111 may comprise a phone connection, and the sound file is delivered to the telephone via the phone connection.

In one embodiment wherein the data receiving device 113 is a computing device, the server computing device 111 may transmit an email to an email account on the data receiving device 113. In another embodiment, the server computing device 111 may comprise a web server, and the server computing device 111 may transmit data indicative of a web page to the computing device that is displayed in a web browser by the computing device. Such web page may display various graphical elements related to the personal health data, including discrete measurements, graphs of characteristics over time or bar charts. For example, the web page may display a graph indicating over time the user's body temperature. While FIG. 1 shows a communication link 112 between the server computing device 111 and the data receiving device 113, the server computing device 111 may also communicate with the data receiving device 113 via the network 110.

Figure 2:
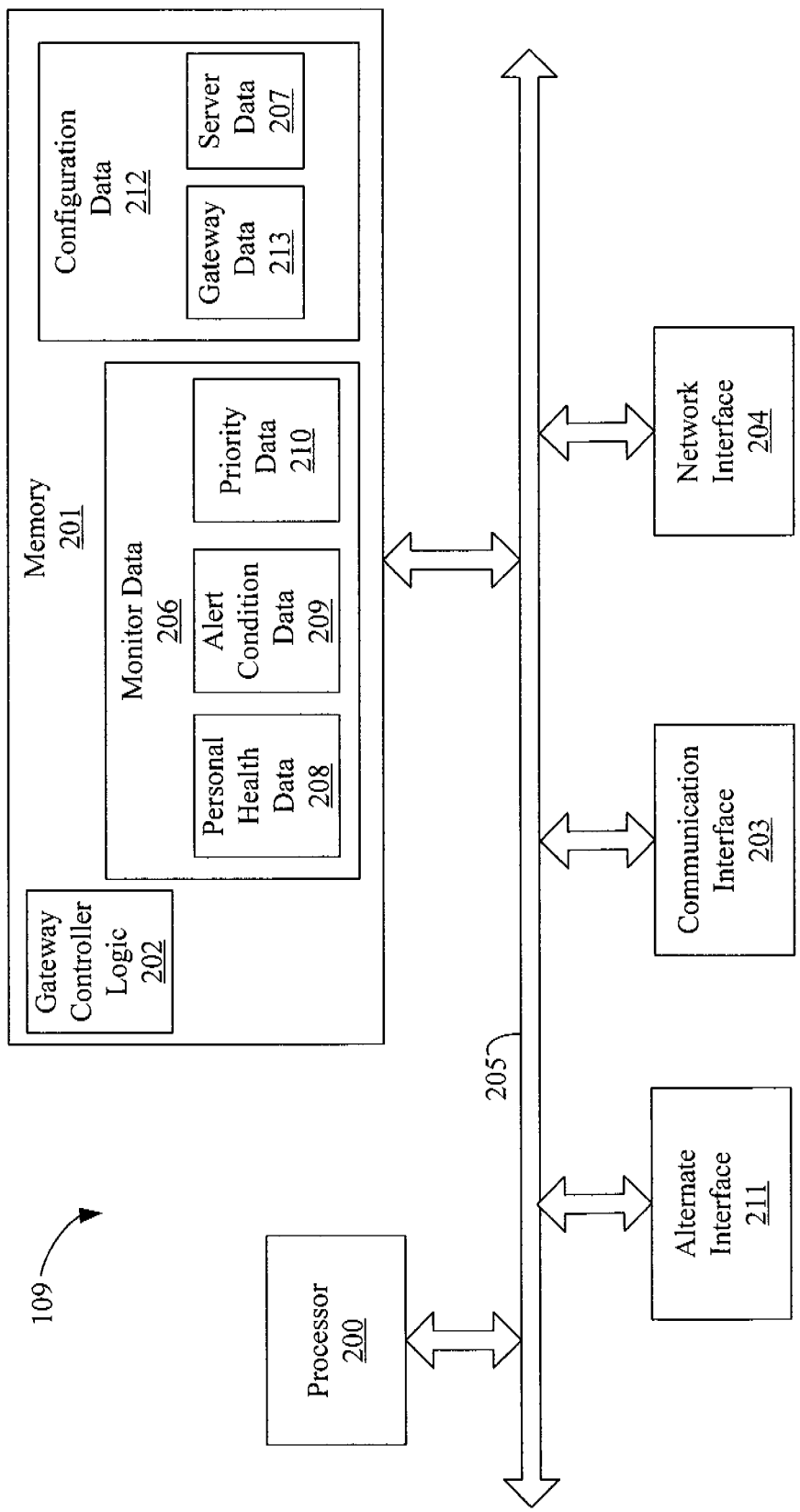
FIG. 2 is a block diagram of a gateway computing device of the system depicted in FIG. 1.

FIG. 2 depicts an exemplary embodiment of the gateway computing device 104. The gateway computing device 104 comprises gateway controller logic 202 for generally controlling the operation and functionality of the gateway computing device 104. In the exemplary embodiment shown by FIG. 2, gateway controller logic 202 is implemented in software and stored in memory 201. In other embodiments, the gateway controller logic 202 may be implemented in firmware, hardware, or any combination of software, firmware, and/or hardware.

The exemplary embodiment of the gateway computing device 104 depicted by FIG. 2 includes a processor 200, which comprises processing hardware for executing instructions stored in memory 201. The processor 200 communicates to and drives the other elements within the gateway computing device 104 via a local interface 205, which can include at least one bus.

Furthermore, the gateway computing device 104 comprises a communication interface 203, a network interface 204, and a alternate interface 211. The communication interface 203 may be any type of communication device that communicatively couples the gateway computing device 104 with the monitors 101-104 (FIG. 1) over the communication links 105-108, respectively. Additionally, the network interface 204 may be any type of communication device that communicatively couples the gateway computing device 104 with the network 110 (FIG. 1). Further, the alternate backup interface 211 may be any type of communication device that connects the gateway computing device 109 to the server computing device 109. In one embodiment, the alternate network interface 211 can be an analog dial-up modem, a cellular modern, or a digital subscriber line (DSL) modem. The analog dial-up modem would connect the gateway computing device 109 to a standard phone line. The cellular modem would connect the gateway computing device 109 to the server computing device 111 via a cellular network. The DSL modem would connect the gateway computing device 109 to a DSL line.

The gateway computing device 109 further comprises monitor data 206 stored in memory 201. The monitor data 206 comprises data received by the monitoring devices 101-104 (FIG. 1) and transmitted to the gateway computing device 109. Such data may include personal health data 208 and/or alert condition data 209. Note that each transmission of personal health data 208 or alert condition data 209 from a monitor 101-104 comprises a unique identifier, which is data uniquely identifying each of the monitors 101-104 and/or the user registered with the server computing device 111 (FIG. 1). An exemplary registration process is described in more detail herein.

Note that the personal health data 208 is that data that is periodically and during the ordinary course transmitted to the gateway computing device 109 by the monitors 101-104. Such personal health data 208 can be for example data received from the chest strap 101 (FIG. 1) indicative of the user's heart rate, respiration, muscle activity, oxygen saturation (SpO2), and/or galvanic skin response (GSR). In addition, the personal health data 208 may include data indicative of caloric expenditure or energy expenditure, number of daily steps, and data indicative of sleep/wake patterns. In addition, the personal health data 208 may include data indicative of a glucose measurement received from the glucose monitor 102, a blood pressure or pulse measurement received from the blood pressure monitor 103, or a weight measurement received from the weight monitor 104. Note that the term periodically can refer to any interval at which the personal health data 208 is transmitted to the gateway computing device 109. Periodically can refer to a set interval, e.g., every five minutes, or the personal health data can be transmitted at random intervals. As additional examples, the personal health data 208 may comprise Further alert condition data 209 may include any data that indicates any event that that occurs with respect to one of the monitors 101-104 or the user. Events for which alert condition data 209 may be generated and transmitted to the gateway computing device 109 by the monitors include, but are not limited to, battery charge complete, battery unplugged, battery plugged, battery critically low, monitor enabled, monitor disabled, the user has fallen, the user has actuated the panic button located on the wearable device monitor 101. In addition, the alert condition data 209 may include data indicative of events that occur related to the gateway computing device. For example, the alert condition data 109 may include data indicating that the gateway computing device reset button (not shown) has been actuated, the gateway computing device 109 is offline, or the gateway computing device 109 is online.

In addition, the gateway computing device 109 comprises configuration data 212 stored in memory 201. The configuration data 212 may be any data needed for the operation of the gateway computing device 109. For example, the configuration data 212 may comprise server data 207. The server data 207 stores data indicative of the universal resource locator (URL) of the server computing device 111. In one embodiment, the URL is an Internet address for example. In operation, the gateway controller logic 202 uses this URL to communicate with the server computing device 111 for registration, which is described further herein, to transmit personal health data, to transmit alert data, or to query the server computing device 111 for management commands such as firmware upgrades or to make configuration changes of the gateway computing device 109. In one embodiment, the gateway computing device 109 may store as server data 207 a plurality of URLs to segregate the different type data. For example, there may be one URL to which routine periodic personal health data is transmitted, and there may be a different URL to which alert condition data is transmitted. In such an embodiment, the server computing device 111 may span multiple physical computing devices as is sometimes the case in distributed, networked Internet-based applications.

In another embodiment the gateway computing device 109, the server data 207 may store multiple redundant URLs for the same type of data. In such an embodiment, the server computing device 111 would comprise multiple physical separate computing devices, each with a different URL. For example, the gateway computing device 109 may store multiple addresses for alert condition data. Given the severity of the information delivered in this instance, this would allow multiple (physically and geographically distinct) server computing devices 111 to process the alert condition data in parallel making the application fault tolerant to a fault occurring on one of the server computing devices 111. In such an embodiment, database synchronization techniques well-known to those skilled in the art are used to synchronize the server database 307 with another database on another server computing device when such a fault.

In addition, the configuration data 212 comprises gateway data 213. The gateway data 213 comprises data for controlling the gateway computing device. For example, the gateway data 213 may comprise a media access control (Mac) address data identifying the gateway computing device 109. In addition, the gateway data 213 may comprise a serial number of the gateway computing device 109. The gateway data 213 may further comprise a flag for enabling or disabling a buzzer located on the gateway computing device 109. Additionally, the gateway data 213 may comprise a light emitting diode (LED) test flag for indicating that an LED test is to be performed at start up.

In one embodiment, the gateway computing device 109 may be a cellular telephone or other mobile network device, e.g., a PDA. In such an embodiment, the monitors 101-104 would communicate with the cellular telephone or other mobile device, and the cellular telephone or other mobile device would communicate with the server computing device 111. In this regard, the gateway controller logic 202 would be ported to run on the cellular telephone or other mobile device.

In another embodiment, both the gateway computing device 109 and a mobile network access device such as a cellular telephone could coexist as redundant access devices. In such a case, the wearable device monitor 101 would recognize when it has left range of the gateway computing device 109. U.S. patent application Ser. No. 11/972,275 entitled "Wireless Sensor Network Data Management System and Method" filed on Jan. 10, 2008, which is incorporated herein by reference, discloses a method for detecting the presence of the gateway computing device 109. In such a case, the wearable device monitor 101 autonomously chooses to access the network via the gateway computing device 109 or the mobile network access device (such as a cellular telephone). In such an embodiment, the access devices could be prioritized such that lower power or lower cost (in terms of real financial costs associated with accessing the network e.g. air time) would be first preference access.

From time-to-time, the gateway computing device 109 may lose connectivity with the server computing device 111. In such a scenario, the gateway computing device 109 detects such loss in connectivity and defers transmission of personal health data 208 and alert condition data 209 until connectivity is restored with the server computing device 111.

In one embodiment of the present disclosure, the gateway computing device 109 may prioritize alert condition data 209 received from the monitors 101-104 and store such prioritized alert condition data 209 as priority data 210. In this regard, as described above, the alert condition data 209 received from the monitors 101-104 comprises a unique identifier(s) and data indicative of the event that resulted in the alert condition data being sent to the gateway computing device 109. Such events may be predetermined to have a particular priority. For example, certain events may have "Immediate," "High," "Medium," or "Low" priority. While "Immediate," "High," "Medium," or "Low" priority are described as exemplary priority types, other priority types may be used in other embodiments, and such types may be configurable.

To prioritize the alert condition data 209, the gateway controller logic 202 compares the data indicative of the event that resulted in the alert condition data 209 being sent to the gateway computing device 109 to data indicative of one or more events that are associated with an "Immediate" priority. For example, events that are associated with an "Immediate" priority may be a fall by the user, the panic button on the chest strap 101 was actuated, or the gateway computing device 109 reset button (not shown) was actuated. If the alert condition data 209 received from the monitor 101 comprises data that indicates "Immediate" priority, the gateway controller logic 202 stores as priority data 210 the alert condition data 209 correlated with an identifier that indicates that the alert condition data 209 has "Immediate" priority. If the alert condition data 209 has "Immediate" priority, the gateway controller logic 202 immediately transmits a repackaged data packet of the alert condition data 209 to the server computing device 111.

In addition, the gateway controller logic 202 compares the data indicative of the event that resulted in the alert condition data 209 being sent to the gateway computing device 109 to data indicative of one or more events that are associated with a "High" priority. An event that may be "High" priority is the battery is critically low. If the alert condition data 209 received from the monitor 101 comprises data that indicates "High" priority, the gateway controller logic 202 stores as priority data 210 the alert condition data 209 correlated with an identifier that indicates that the alert condition data 209 has "High" priority.

In addition, the gateway controller logic 202 compares the data indicative of the event that resulted in the alert condition data 209 being sent to the gateway computing device 109 to data indicative of one or more events that are associated with a "Medium" priority. An event that may be "Medium" priority is the strap of the monitor 101 has been removed or the strap of the monitor 101 has been fastened, for example. If the alert condition data 209 received from the monitor 101 comprises data that indicates "Medium" priority, the gateway controller logic 202 stores as priority data 210 the alert condition data 209 correlated with an identifier that indicates that the alert condition data 209 has "Medium" priority.

In addition, the gateway controller logic 202 compares the data indicative of the event that resulted in the alert condition data 209 being sent to the gateway computing device 109 to data indicative of one or more events that are associated with a "Low" priority. An event that may be "Low" priority is the battery is unplugged, the battery is plugged, and the battery charge is complete. If the alert condition data 209 received from the monitor 101 comprises data that indicates "Low" priority, the gateway controller logic 202 stores as priority data 210 the alert condition data 209 correlated with an identifier that indicates that the alert condition data 209 has "Low" priority.

As described above, the gateway computing device 109 may lose connectivity with the server computing device 111. When connectivity is lost and alert condition data 209 has been prioritized and stored as priority data 210, upon regaining connectivity with the server computing device 111, the gateway computing device 109 transmits data have a higher correlated priority first. In this regard, alert condition data that is correlated in the priority data 210 as "Immediate" priority is transmitted before alert condition data 209 that is correlated in the priority data with "High," "Medium," and "Low" priority levels.

Figure 3:
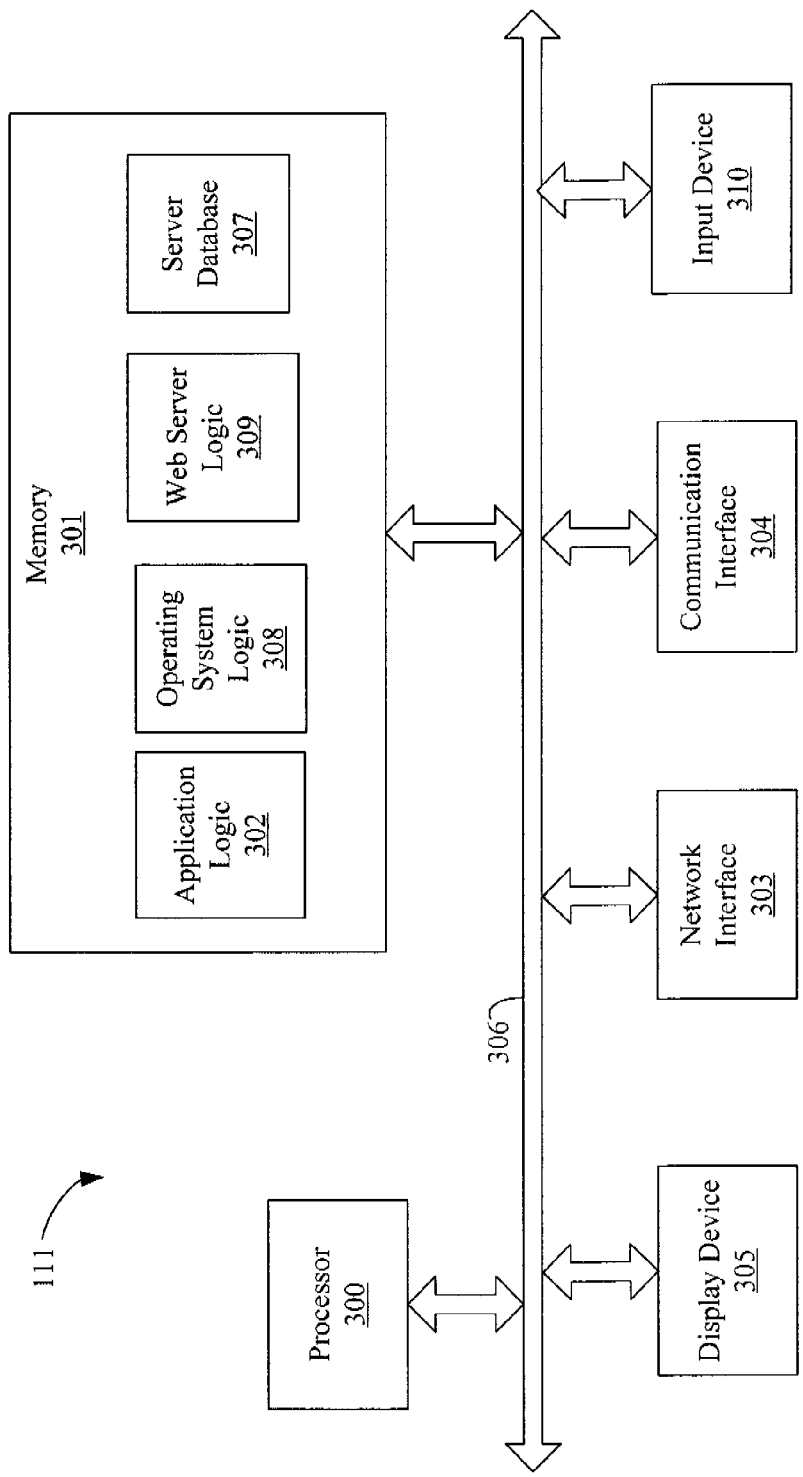
FIG. 3 is a block diagram of a server computing device of the system depicted in FIG. 1.

FIG. 3 depicts an exemplary embodiment of the server computing device 111. The server computing device 111 comprises application logic 302 for generally controlling the operation and functionality of the server computing device 111. In the exemplary embodiment shown by FIG. 3, application logic 302 is implemented in software and stored in memory 301. In other embodiments, the application logic 302 may be implemented in firmware, hardware, or any combination of software, firmware, and/or hardware. In one embodiment, the application logic 302 is developed using any web framework known in the art or future-developed. As a non-limiting example, the application logic 302 may be developed using the Ruby programming language, a Representational State Transfer (REST) web service, and the Ruby on Rails web framework.

The server computing device 111 further comprises operating system logic 308 stored in memory 301. The operating system logic 308 controls the execution of computer programs, such as application logic 302 and provides scheduling, input-output control, file and data management, memory management, and communication control and related services. Exemplary operating systems include, but are not limited to Windows® Server, Linux®, and Unix®.

The server computing device 111 further comprises a server database 307 stored in memory 301. The server database 307 stores data identifying users and corresponding monitors. In addition, the server database 307 stores personal health data 208 (FIG. 2) and alert condition data 209 (FIG. 2) associated with each user and with each monitor correlated with each user. In this regard, each data packet received from the gateway computing device 109 (FIG. 1) comprises a unique identifier, which can be the user identifier, the monitor identifier or both. The server computing device 111 stores the personal health data 208 and the alert condition data 109 received in the data packets in the server database 307 correlated with the user or monitor identified in the data packet. Note that the server database 307 may be any type of database known in the art or future-developed, and may include Oracle, Microsoft structured query language server (SQLServer), MySQL, and PostgreSQL.

The server computing device 111 further comprises web server logic 309. The web server logic 309 generates data indicative of a web page and delivers the data to a remote computing device, which displays the web page defined by the data received. Exemplary web servers include, but are not limited to, Apache, Litespeed, and Information Internet Services (IIS).

The exemplary embodiment of the server computing device 111 depicted by FIG. 2 includes a processor 300, which comprises processing hardware for executing instructions stored in memory 301. The processor 300 communicates to and drives the other elements within the server computing device 111 via a local interface 306, which can include at least one bus.

Furthermore, the server computing device 111 comprises a network interface 303 and a communication interface 304. The network interface 303 may be any type of communication device that communicatively couples the server computing device 111 with the network 110 (FIG. 1). Additionally, the communication interface 304 may be any type of communication device that communicatively couples the server computing device 111 with the data receiving device 113 (FIG. 1). In one embodiment, the server computing device 111 can connect to the data receiving device 113 via the communication interface 304 or the network interface 303 via the Internet.

In addition, the server computing device 111 comprises a display device 305. The display device 305 may be any type of display device known in the art or future-developed. As a mere example, the display device 305 may be a liquid crystal display (LCD).

Furthermore, the server computing device 111 comprises an input device 310. The input device 310 may be, for example, a keyboard.

An exemplary operation of the monitoring system 100 will now be described below. It is to be understood that changes and modifications to the described operation are possible.

As indicated hereinabove with reference to FIG. 1, the user (not shown) of the monitors 101-104 (FIG. 1) registers with the monitoring system 100. The registration associates the monitors 101-104 with a user identifier. In this regard, when the monitors 101-104 are powered on upon initial use by the user, the monitors 101-104 transmit a data packet (not shown) to the gateway computing device 109. In one embodiment, the data packet transmitted to the gateway computing device 109 by each of the monitors upon initial use comprises an identifier that uniquely defines the individual monitor such as the monitor's serial number, which is assigned to and stored in the monitor 101-104 during the manufacturing process.

The gateway computing device 109 receives the data packets from each of the monitors 101-104. Upon receipt of the data packets from each of the monitors, the gateway controller logic 202 (FIG. 2) stores as monitor data 206 each data packet, which includes the monitors' serial numbers. The gateway computing device 109 repackages the stored data packets into a network deliverable format (e.g., transmission control protocol/Internet protocol (TCP/IP), encapsulated hypertext transfer protocol (HTTP), or extensible markup language (XML) packets) and transmits the repackaged data packets to the server computing device 111.

The server computing device 111 receives the data packets via the network 110. As indicated above, in one embodiment, each data packet received comprises a monitor serial number. The application logic 302 (FIG. 3) generates a user identifier, which can be a unique integer associated with the user of the monitors 101-104. In addition, the application logic 302 generates a monitor identifier for each monitor serial number received. The monitor identifier uniquely identifies the monitor 101-104, and such monitor identifier may, in one embodiment, incorporate the monitor's serial number. However, in other embodiments, the monitor identifier may be randomly generated numbers that are associated with each monitor. The application logic 302 stores in the server database 307 the generated user identifier correlated with each generated monitor identifier. Indeed, for each user identifier there is one or more monitor identifiers stored correlated with the user identifier.

After generation of the user identifier and the monitor identifier for each monitor, the application logic 302 transmits via the network interface 303 (FIG. 3) over the network 110 the user identifier and the monitor identifiers to the gateway computing device 109. The gateway computing device 109 receives the user identifier and the monitor identifiers and stores the user identifier and the monitor identifiers as monitor data 206.

The gateway controller logic 202 then transmits to each monitor 101-104 the user identifier and the monitor's respective monitor identifiers. Each monitor is considered registered once it has received the user identifier and the monitor identifier. The monitors 101-104 store the user identifier and respective monitor identifier locally on the monitor 101-104.

As will be described further herein, each subsequent transmission by a monitor 101-104 of personal health data 208 (FIG. 2) or alert condition data 209 (FIG. 2) will contain the user identifier, the monitor identifier or both. If the monitor identifiers or user identifier are lost from the monitor 101-104, the monitor 101-104 will automatically request a new user identifier and monitor identifier using its serial number, as described above.

Once registration is completed, the monitors 101-104 are then operational. In this regard, the monitors 101-104 from time-to-time capture personal health data and store the personal health data on the monitor 101-104. The monitors 101-104 package the captured data into data packets and transmit the data packets to the gateway computing device 109 via communication links 105-108, as described above. Note that the personal health data packets transmitted by the monitors 101-104 each comprise the user identifier, the monitor identifier, or both, and the personal health data. In one embodiment, a separate monitor identifier and user identifier may be used so that multiple users can use the same monitor 101-104 or the user can have multiple monitors 101-104.

In addition to periodically capturing personal health data 208, the monitors 101-104 may also capture alert condition data 209, as described above. In such a scenario, the monitors 101-104 would also package data indicative of the alert condition data 209 into a data packet and transmit the data packet to the gateway computing device 109. Note that the alert condition data packets transmitted would also each comprise the user identifier, the monitor identifier, or both and the alert condition data.

Note that in repackaging the personal health data 208, the alert condition data 209, and the unique identifiers contained in the received data packets, the gateway controller logic 202 uses encryption to encrypt the repackaged data packets. In this regard, the gateway controller logic 202 may use secure socket layer (SSL) encryption. In addition, the gateway controller logic 202 may use other encryption or security methods known in the art or future-developed to secure the data packets that are sent via network 110 to the server computing device 110.

The gateway controller logic 202 receives the data packets from the monitors 101-104 via the communication interface 203 over the communication links 105-108, respectively. The gateway controller logic 202 stores the data packets as monitor data 206. The gateway controller logic 202 then repackages the data packets, comprising the unique identifier and the personal health data, into a network deliverable format (e.g., TCP/IP, encapsulated HTTP, and XML packets) and transmits the data packets to the server computing device 111 via the network interface 204 over the network 110. In one embodiment, the data packets transmitted by the gateway controller logic 202 conform to a communication protocol such as the REST web service described above. Note that when the data packets are repackaged by the gateway controller logic 202, the data packets retain the unique user identifier, monitor identifier, or both.

The gateway controller logic 202 periodically transmits the repackaged data packets comprising personal health data 208 to the server computing device 111 (FIG. 1). Note that the term periodically can refer to any interval at which the personal health data or alert condition data is transmitted to the server computing device 111. Periodically can refer to a set interval or the personal health data can be transmitted at random intervals. For example, the gateway controller logic 202 may transmit data packets received from the monitors 101-104 every fifteen minutes to the server computing device 111.

In one embodiment, the gateway controller logic 202 determines whether the data packet contains alert condition data 209. For example, the data packet may comprise the unique identifier and data indicating that the user has fallen. In such a scenario, the gateway controller logic 202 would not wait for the periodic transmission time, e.g., every fifteen minutes, to transmit the repackaged data packet to the server computing device 111. Instead, the gateway controller logic 202 would assign an "Immediate" priority to the data packet, and the gateway controller logic 202 would immediately transmit the repackaged data packet indicating the alert condition data to the server computing device 111.

Further, as described above, the gateway controller logic 202 may also prioritize alert condition data 209 based upon the type of event that is included in the data packet received from the monitors 101-104. The gateway computing device 109 may then transmit the repackaged data packets of the alert condition data 209 based upon the priority level assigned to the alert condition data 209.

The application logic 302 receives the data packets from the gateway computing device 109 via the network interface 304 over the network 110. As noted hereinabove, the data packet may comprise data indicative of the personal health data 208 (FIG. 2) or alert condition data 209 (FIG. 2). When the data packet comprises personal health data 208, the application logic 302 stores the personal health data 208 (FIG. 2) in each data packet in the server database 307 correlated with the user identifier and/or monitor identifier previously stored in the server database 307 during registration.

When the data packet comprises alert condition data, the application logic 302 may assign a type identifier to the alert condition. A type identifier identifies the type of alert condition that is contained in the data packet, and exemplary type identifiers include "NORMAL," "CAUTION," or "SEVERE." In this regard, the application logic 302 may assign a "NORMAL" identifier to the alert condition data 209 (FIG. 2) if the data packet comprises data indicating the battery of the wearable device monitor 101 (FIG. 1) is fully charged or the gateway computing device 109 (FIG. 1) is online. In addition, the application logic 302 may assign a "CAUTION" identifier to the alert condition data 209 if the data packet comprises data indicating the battery is critically low or the gateway computing device 109 is offline. Furthermore, the application logic 302 may assign a "SEVERE" identifier to the alert condition data 209 if the data packet comprises data indicating the user fell.

After determining the identifier type for the data packet comprising alert condition data 209, the application logic 302 stores data indicative of an alert condition and the type identifier assigned to the alert condition data 209 correlated with the user identifier and/or monitor identifier in the server database 307.

Note that in one embodiment the application logic 302 manages a plurality of users (not shown) (i.e. human subjects being monitored), manages a plurality of devices 101-104 (FIG. 1), receives periodic personal health data, receives asynchronous event and/or alert data, receives monitor status information, and stores data indicative of each of these into the server database 307. In addition, the application logic 302 formats and supplies data in the form of a graphical user interface to users and their caregivers, extracting pertinent event data and presenting this via the graphical user interface (GUI) and/or via e-mail messages and/or via SMS text messages to a cellular telephone.

In one embodiment of the monitoring system 100, the application logic 302 displays to the display device 305 (or may generate a web page that is displayed to a computing device of a data receiving device 113) a graphical user interface (GUI) comprising graphical elements relaying the personal health data and alert condition data received from the monitors 101-104. In this regard, the application logic 302 may display discrete readings from a monitor 101-104. For example, the application logic 302 may display a user's glucose reading at a particular time. Additionally, the application logic 302 may display graphical elements that show personal health data over time. For example, the application logic 302 may display a graph of the user's body temperature over a particular period of time, e.g., the last twenty-four hours. As another example, the application logic 302 may display heart rate measurements in a line chart showing the measurements over a particular period of time. In other embodiments, other types of graphical elements may be used to convey the personal health data collected by the application logic 302 and stored in the server database 307.

As described above, the monitoring system 100 may be used to collect continuous and periodic personal health data. As further described above, particular events indicating alert conditions may also be detected by the monitors 101-104, and alert condition data indicating the alert conditions may be transmitted to the server computing device 111, as described above. As an example, a user wearing the chest monitor 101 (FIG. 1) may fall, which would be an alert condition. In such a scenario, the gateway computing device 109 receives a data packet from the chest monitor 101 comprising data indicating the user identifier and/or monitor identifier and an alert condition.

As described above, upon receipt of the data packet indicating the alert condition, the gateway computing device 109 would repackage the data packet, as described above, and transmit a data packet to the server computing device 111 indicating the user identifier and/or monitor identifier and an alert condition, i.e., a fall. Upon receipt of the data packet, the application logic 302 would immediately transmit a notification of the alert condition to the data receiving device 113 (FIG. 1). Such a notification may be sent to recipients of the alerts including but not limited to SMS text message, e-mail, and web services such as REST, SOAP, and WSDL. Such recipients may include, but are not limited to, caregivers, call centers, administrators, personal health records, social networking services, and clinicians.

In one embodiment, the application logic 302 may also generate alert conditions by periodically monitoring the server database 307 for alert states. For example, the application logic 302 may periodically retrieve heart rate data and compare the heart rate data to a threshold value. If the heart rate data retrieved from the server database 307 exceeds the threshold value, then the application logic 302 may transmit a notification as described above.

In one embodiment, the server computing device 111 also generates alert conditions by monitoring data packets received from the gateway computing device 109 or monitoring the server database 307. In such an embodiment, the application logic 302 may invoke an operating system process or thread to poll the server database 307 for alert states such as, but not limited to threshold detection of heart rate. As an example, a Command Run On (cron) job is periodically executed on the server computing device 111. The cron job launches some form of executable code, such as a script. The script calls the application logic 302 which then queries the server database 307 to determine if there is alert condition, e.g., the heart rate or other measurement, has exceeded a certain threshold. the gateway computing device 109 is offline, or the gateway computing device 109 is out of range. If there is an alert condition, the server computing device 111 automatically and immediately transmits data indicative of the alert to the data receiving device 113.

Moreover, the server computing device 111 may further recognize priority of certain types of personal health data and alert conditions. As an example, a user falling may result in an immediate alert to a data receiving device 113. In one embodiment, the immediate alert is delivered in the same operating system process spawned immediately by the critical event data received from the gateway computing device 109.

In one embodiment, the server computing device 111 may queue non critical events. In this regard, an operating system process may be triggered by a data packet received from the gateway computing device 109. If the data packet indicates a noncritical event, data indicative of the event may be delivered later by a background operating system process. Such a scheme maximizes server resources such as physical memory and processor bandwidth while delivering critical events in the most immediate fashion possible.

In one embodiment, the gateway computing device 109 further comprises a dial up connection, in addition to the network interface 204 that connects the gateway computing device 109 with the server computing device 111. If connectivity is down over the network 110, the gateway computing device 109 may establish connection with the server computing device 109 via the alternate interface 211, thus serving as a backup. In addition, the alternate interface 211 may serve as a redundant connection to the server computing device 111. In this regard, if the gateway computing device 109 receives alert condition data 209, the gateway controller logic 202 may simultaneously send the alert condition data 209 via the network interface 204 and the alternate interface 211. In one embodiment, the alternate interface 211 may also be used to transmit personal health data 208 having a low priority. However, in other embodiments, the dial-up connection may only be used to transmit alert condition data having a higher priority, e.g., the user has fallen.

In addition, the gateway computing device 109 may lose communication with the monitors 101-104 (FIG. 1). For example, the monitors 101-104 may be out of range of the gateway computing device 109. In this regard, the gateway controller logic 202 periodically (e.g., every second or at random intervals) transmits a signal to the monitors 101-104, and the signal (not shown) includes a timestamp. Such signal is hereinafter referred to as a beacon signal. In response to receiving the beacon signal, the monitors 101-104 transmit a response signal (not shown) to the gateway computing device 109 that also includes a timestamp indicating the time that the monitor 101-104 responds to the beacon signal. Thus, the gateway controller logic 202 can calculate a latency time period, which is the time difference between when the beacon signal is sent and when the monitor 101-104 responds. If the monitor 101-104 does not respond, such lack of response indicates to the gateway computing device 109 that the monitor 101-104 is out of range of the gateway computing device 109.

In such a scenario, the gateway controller logic 202 determines that there is no communication with the monitors 101-104, and data packets are not being received from the monitors 101-104. If the gateway computing device 109 is no longer receiving data packets from the monitors 101-104, the gateway controller logic 202 transmits a data packet to the server computing device 111 comprising data indicating that one or more of the monitors 101-104 are out of range. If the server computing device 111 receives a data packet indicating that one of the monitors 101-104 is out of range, the server computing device 111 may display to the display device 305 data indicating that the monitor 101-104 is out of range. Note that the out of range alert may also be generated by a background process, e.g., a cron job as described above, of the server computing device 111.

Additionally, the monitor 101-104 that is out of range detects that it is no longer in communication with the gateway computing device 109 when the beacon signal is not received from the gateway computing device 109. When the monitor 101-104 detects that it is no longer in range of the gateway computing device 109, the monitor 101-104 continues to collect personal health data 208 (FIG. 2) and alert condition data 209 (FIG. 2) from the user of the monitors 101-104. The monitors 101-104 store in memory (not shown) on the monitors 101-104 data collected during the period in which the monitor 101-104 is out of range of the gateway computing device 109. The storing in memory of the data collected is referred to as "buffering."

Subsequently, the monitor 101-104 may then become within range of the gateway computing device 109, which the monitor 101-104 determines when it finally receives a beacon signal from the gateway computing device 109. In response, the monitor 101-104 transmits to the gateway computing device 109 all the personal health data 208 and alert condition data 109 that was collected during the period in which the monitor 101-104 was out of range of the gateway computing device 109. In this regard, the monitor 101-104 transmits data packets comprising the personal health data 209 and the alert condition data 209 collected during the time that the monitor 101-104 was not in range of the gateway computing device 109. In response, the gateway controller logic 202 repackages each of the data packets received once communication between the monitor 101-104 and the gateway computing device 109 is reestablished and transmits all the data packets to the server computing device 111. Notably, the gateway controller logic 202 can bundle all the data packets into a single data packet for a single transmission. In this regard, the bundled data packets are a concatenation of each individual data packet. For example, if JavaScript object notation (JSON) or XML POST are used in the transmission of data packets to the server computing device, then the bundled data packets are a concatenation of each individual JSON or XML POST.

Once the server computing device 111 determines that data packets are now being sent from the gateway computing device 109 and the monitors 101-104 are now in range of the gateway computing device 109, the server computing device 111 further displays data to the display device 305 (or to a web page being displayed by the web server 309) indicating that the monitor 101-104 is now in range. In addition, the server computing device 111 unbundles the personal health data 208 and the alert condition data 209 from the data packets received and stores the personal health data 208 and the alert condition data 209 in the server database 307 correlated with the user identified in the data packet's unique identifier.

Note that the home gateway computing device 109 gateway communicates with the server in two ways. The primary method is via the network interface 204 (FIG. 2) over the Ethernet. In this regard, typically the gateway computing device 109 communicates with the server computing device 111 via the network interface 204 over a Broadband connection such as digital subscriber line (DSL) or cable modem.

In the event Ethernet connection via the network interface 204 is not available, the gateway computing device 109 may communicate with the server computing device 111 via the alternate interface 211 (FIG. 1) and effectively replace the Ethernet connection. In this regard, the gateway computing device 109 may either communicate via the network interface 204 over the Ethernet or via the alternate interface 211 over a standard telephone line, for example. In addition, the gateway computing device 109 can automatically switch between network interface 204 and the alternate interface 211.

Specifically, the gateway controller logic 202 monitors the physical link, e.g., an Ethernet link, of the network interface 204 at regular intervals. In this regard, the gateway controller logic 202 queries the physical link status of the network interface 204. In one embodiment, the network interface 204 comprises an Ethernet transceiver (not shown). In such an embodiment, the gateway controller logic 202 queries the Ethernet transceiver physical link status. If the query indicates that there is no existing physical link via the interface 204, the gateway controller logic 202 begins to send repackaged data packets through the alternate interface 211, e.g., via the standard phone line.

Additionally, the physical link may be operable but the application layer may be inoperable. Note that in one embodiment, the application layer is HTTP. In operation, the gateway controller logic 202 determines if the application layer is operable. In this regard, the gateway controller logic 202 transmits a request, e.g., an HTTP request, to the server computing device 111. If the application layer is operable, the server computing device 111 transmits an application layer response, e.g., an HTTP response back to the gateway computing device 109. If the application layer response is not received, such nonreceipt indicates to the gateway computing device 109 that the application layer is inoperable. Thus, if the application layer response is not received, the gateway controller logic 202 begins to send repackaged data packets through the alternate interface 211, e.g., via the standard phone line.

Once the gateway controller logic 202 switches to the alternate interface 211, it continues to test the Ethernet connection to determine if it subsequently becomes active. If the Ethernet connection is found to be active the gateway controller logic 202 switches back to Ethernet as the primary connection and transmits data packets through the network interface 204 to the server computing device 211.

If the gateway computing device 109 receives alert condition data 209, the gateway controller logic 202 first attempts to transmit data packets via the last operable connection, i.e., if the most recent operable connection is the network interface 204, the gateway controller logic 202 will transmit data packets via the network interface 204 but if the most recent operable connection is the alternate interface 211 the gateway controller logic 202 will transmit the data packets via the alternate interface 211 If the most recent operable connection is now inoperable, the gateway controller logic 202 will attempt to transmit the data packets over the other connection.

Note that for an emergency response alert condition, e.g., a panic button or a fall, Underwrite Laboratories (UL) standards limit the number of dial attempts that can be made before the gateway computing device 109 must leave a telephone phone line free for a defined length of time. Meanwhile the gateway controller logic 202 continues to monitor the Ethernet connection, and if the connection through the network interface 204 is operable, the gateway controller logic 202 can transmit data packets indicative of alert condition data 209 received from the monitors 101-104.

In addition, UL standards require the gateway computing device 109 to enter a back-off period leaving the telephone line untouched and free for incoming calls following the transmission of personal health data 108 or alert condition data 209. Such a back off period only applies to an emergency response alert condition. Thus, instead of posting subsequent alert condition data 209 as a separate message, all available alert condition data 209 are bundled into a single XML encoded message at the time they are transmitted to the server. The gateway computing device 109 then observes the UL required phone line back-off period. Meanwhile if the user presses the panic button additional times during the back-off period, the alert condition data 209 is stored in a queue in the monitor data 206 and are transmitted as described above after the back-off period has expired.

Because of the encryption and security features of the communication link between the gateway computing device 109 and the server computing device 111, there is a delay between each alert condition data transmission. This produces lengthy delay when transmitting multiple alerts.

Furthermore, in some cases a user of the monitors 101-104 pushes the panic button, described above, multiple times for a single alert situation in a short period of time. The monitor bundles alert condition data indicative of the multiple times the panic button is selected. This bundled multiple data packets comprising alert condition data 209 are transmitted to the gateway computing device 109. In response, the gateway computing device 109 sends a first alert condition data packet to the server computing device 111. In addition, the gateway computing device 109 bundles the remaining multiple alert condition data 209 and transmits the bundled multiple alert condition data to the server computing device 111. Thus, multiple alert condition data 209 must be transmitted to the server computing device 111, and the application logic 302 stores such alert condition data 209 to the server database 307 (FIG. 3), as described above.

A back-off period is also employed on the server computing device 111 to give the gateway computing device 109 enough time to relinquish the telephone line in case of an incoming call. As an example, in response to receiving alert condition data 209, the server computing device 111 may transmit data indicative of the alert condition data 209 to a data receiving device 113 (FIG. 1) for emergency response. As described herein, a periodic background process (e.g., a cron job) implements the back-off period that will delay the delivery of the alert condition data 209 to the data receiving device 113 so that an agent (not shown) monitoring the data receiving device 113 does receive a busy signal while the gateway computing device 109 is still transmitting alert condition data 209 through the telephone line and may be in the process of hanging up the call.

Note that in one embodiment, the data stored in the server database 307 is organized such that the data is user-centric. In such an embodiment, a single separated database table (not shown) representing a user may have relationships to associated physiological, alert, and monitor tables. In this regard, there may be one table describing the user, such as the user's name, address, phone numbers, and other medical information such as allergies, medical conditions, and caregiver information, key location (how to get into the person's house) hospital preference, hospital number, doctor's name, doctor's number, Premises Access (Combination, Lockbox Code, Key Location), door to break into if no key, pet information, medications, medical equipment in the home, diabetes indicator, cancer indicator, seizure indicator, stroke/costovertebral angle (CVA)/Transient Ischemic Attack (TIA), cardiac history, pacemaker indicator, or other additional information, for example, hereinafter referred to as protected health information (PHI). There may be other tables that describe the user's personal health data, i.e., personal health data collected via the monitors 101-104. To ensure privacy specified in standards such as HIPAA, the server database 307 decouples the protected health information (PHI) from other personal health data.

In one embodiment, to promote further security, the server database 307 also allows the user database table which houses the PHI in an encrypted format or on a separate database server with stricter security enforcement such as DES, triple DES, and RC4 for network traffic transferred between the servers on the network.

In one embodiment, the application logic 302 display a GUI (not shown) that comprises a plurality of management commands that can be executed by the gateway computing device 109. Such exemplary management commands include, but are not limited to, information request, reset, firmware upgrade, self test, self test telephone, ranges test start, range test stop, adjust management poll rate in seconds (e.g., 60), change dial up number, username or password, and/or unregister device. Each of the management commands has associated with it a selectable graphical element, e.g., a check box or a radio button. A user or a caregiver can select one or more of the management commands via the selectable graphical elements that the user or caregiver desires to be performed by the gateway computing device 109. The application logic 302 stores such selection of management commands associated with the user identifier and/or monitor identifier in server database 307.

Periodically, the gateway computing device 109 may transmit a query for management commands to the server computing device 111 by beginning a query cycle every 15 minutes (or at a configurable periodic rate). In response, the application logic 302 transmits to the gateway computing device 109 one of the management commands selected by the user or caregiver, which the gateway computing device 109 then performs. For example, if a reset management command is stored in the server database 307 associated with the user identifier of the requesting gateway computing device 109, the application logic 302 transmits the reset command to the gateway computing device 109, and the gateway computing device 109 executes a reset of the gateway computing device 109. As the management commands selected by the user or caregiver is transmitted to the gateway computing device 109, the application logic 302 removes such command from the server database 307.

Note that a query cycle consists of repeated individual queries transmitted in a loop to the server computing device 111. The query cycle ends when the server computing device 111 does not have any management commands to send. Once the query cycle is complete for the particular gateway computing device 109, the gateway computing device 109 will restart the query cycle 15 minutes later.

During a query cycle, the gateway computing device 109 will send an acknowledgement (ACK) after each individual management command is successfully received from the server computing device 111. If the server computing device 111 does not receive the ACK, then the server will to resend the management command in the same query cycle until the management command is successfully received or a maximum threshold of 5 attempts is reached. This is to prevent an infinite loop in case of a failure on network 110 or server computing device 111. If the ACK is received successfully, then the server computing device 111 puts the management command in a pending state in the server database 307, waiting on a "response" (RSP) from the gateway computing device 109 indicating that the management was successfully executed. When the gateway computing device 109 confirms sends the RSP, the server computing device 111 will completely remove the management command from the server database 307, as described herein. If an RSP is not received by the server computing device 111, it will send the management command on the next query cycle. The RSP will also contain contextual info on the result of the management command such as software version numbers in the case of a firmware upgrade management command. Also, the server computing device 111 will not allow management command of the same type to be transmitted to the gateway computing device 109.

Figure 4:
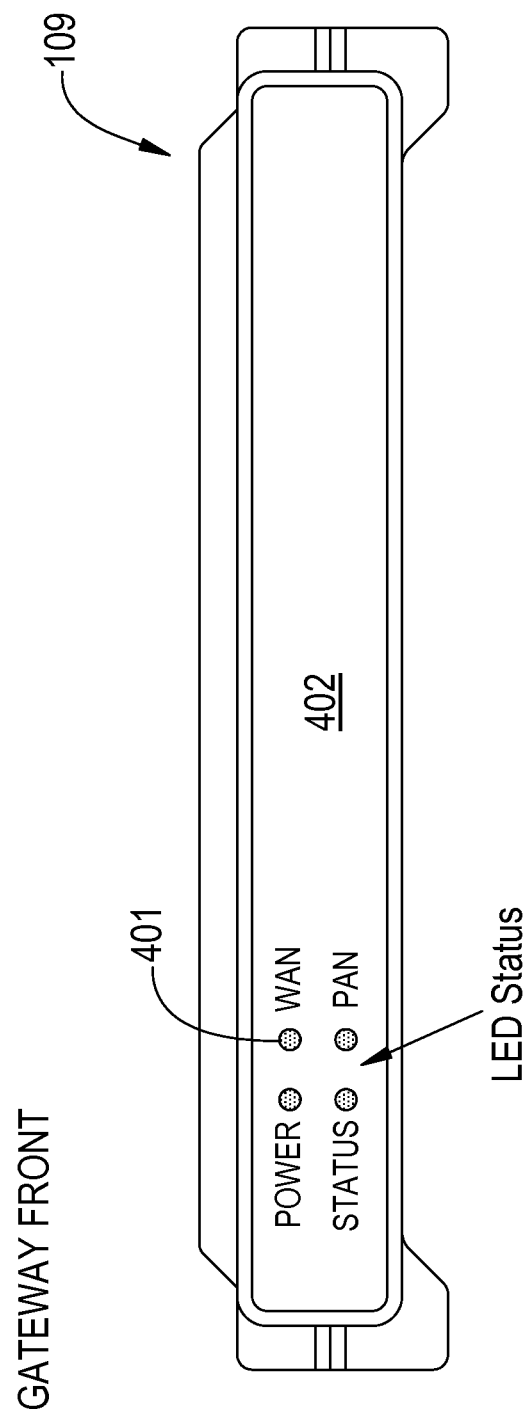
FIG. 4 is a front view of an exemplary gateway computing device depicted in FIG. 2.

FIG. 4 is a front view of an exemplary gateway computing device 109 in accordance with an embodiment of the present disclosure. In such an embodiment, the gateway computing device 109 comprises a front panel 402. The gateway computing device 109 comprises LED status indicators 401 on the front panel 402 for indicating status, battery level indication, charge indication, range indication, and indication of when an alert is detected.

Figure 5:
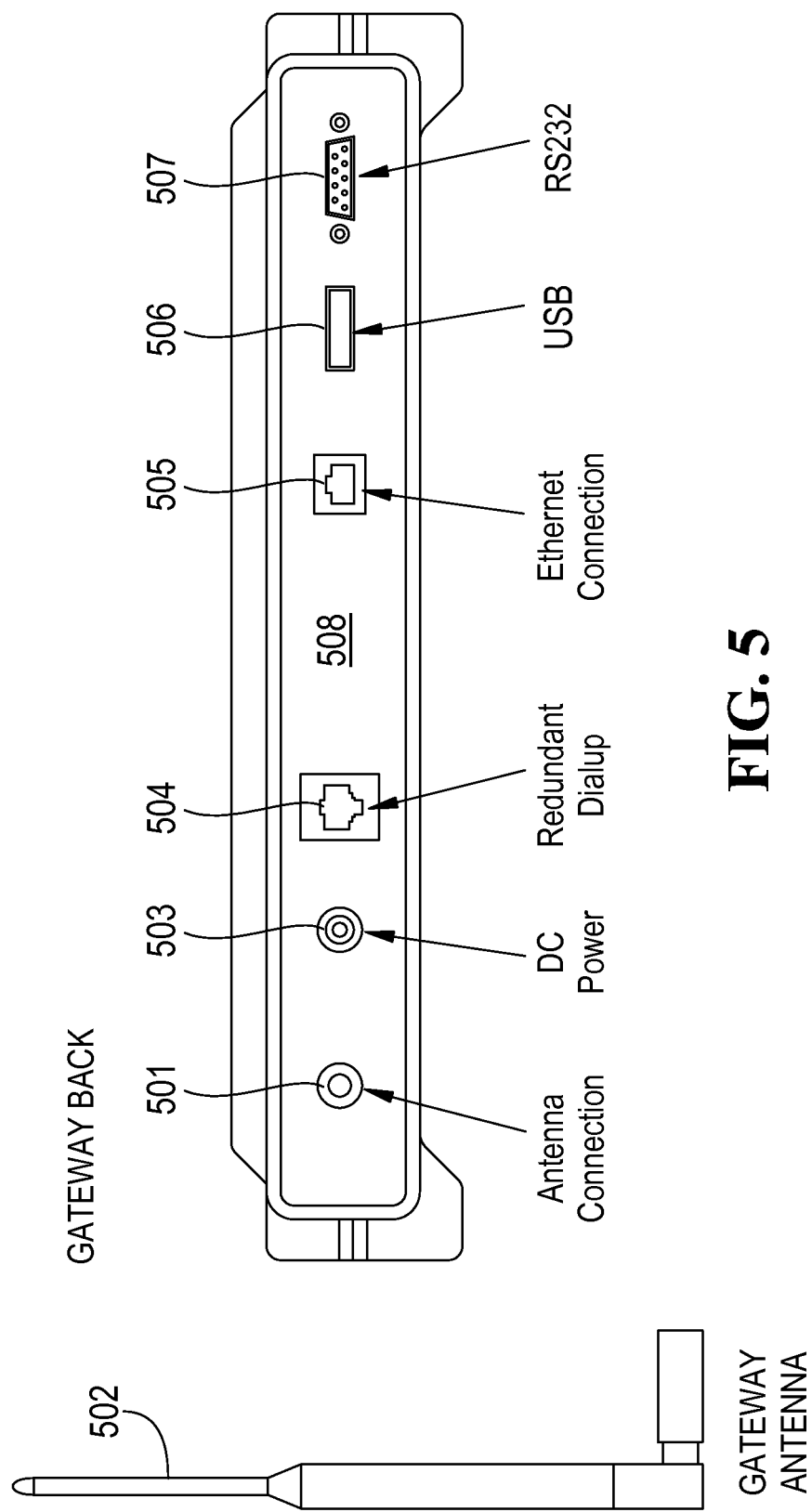
FIG. 5 is a back view of an exemplary gateway computing device depicted in FIG. 2.

FIG. 5 is a back view of the exemplary gateway computing device 109 depicted in FIG. 4. On the back panel 508, the gateway computing device 109 further comprises an external antenna 502 for communicating with the monitors 101-104 (FIG. 1). The gateway computing device 109 further comprises a connection 501 for connecting the antenna 502, a connection 503 for receiving a power source, and an Ethernet connection 505 for connecting to the Internet and communicating with the server computing device 111. In addition, the gateway computing device 109 further comprises a dial backup connection 504 for redundant connections when the primary Internet connection is unavailable and a USB connection 506 for communicating with monitors 101-104 that may not be wireless.

In addition, on the back panel 508 is an RS232 connection 507 for management and configuration. In this regard, a laptop (not shown) may connect to the gateway computing device 109 via the RS232 connection 507. A command line interface on the laptop may allow a user of the laptop to change settings, or otherwise manage the setup of the gateway computing device 109. For example, server computing device URLs can be added or modified via the RS232 connection via the laptop.

Also, the gateway computing device 109 supports reverse secure shell (SSH). SSH includes a command line interface into the gateway computing device 109 through server computing device 111 or any other computing device (not shown) that is communicatively coupled to the network 110. Via the command line interface, a user may initiate commands for changing configuration data 212 (FIG. 2) of the gateway computing device 109. For example, server computing device URLs can be added or modified via the SSH.

In another embodiment, the gateway computing device 109 comprises Firewire for communicating with other devices. Firewire is a standardized format, described in IEEE 1394. The IEEE 1394 interface is a serial bus interface standard for high-speed communications and isochronous real-time data transfer, frequently used by personal computers, as well as in digital audio, digital video, automotive, and aeronautics applications. Such other devices that the Firewire may connect to may include any of the monitors 101-104.

In another embodiment, the gateway computing device 109 comprises Wi-Fi capability as a primary Internet connection in lieu of Ethernet connection 505. In another embodiment, the gateway computing device 109 includes a cellular connection in place of either the Ethernet connection 505 or dialup connection 504. In another embodiment, the gateway computing device 109 comprises a battery backup to provide persistent operation in spite of loss of power.

Figure 6:
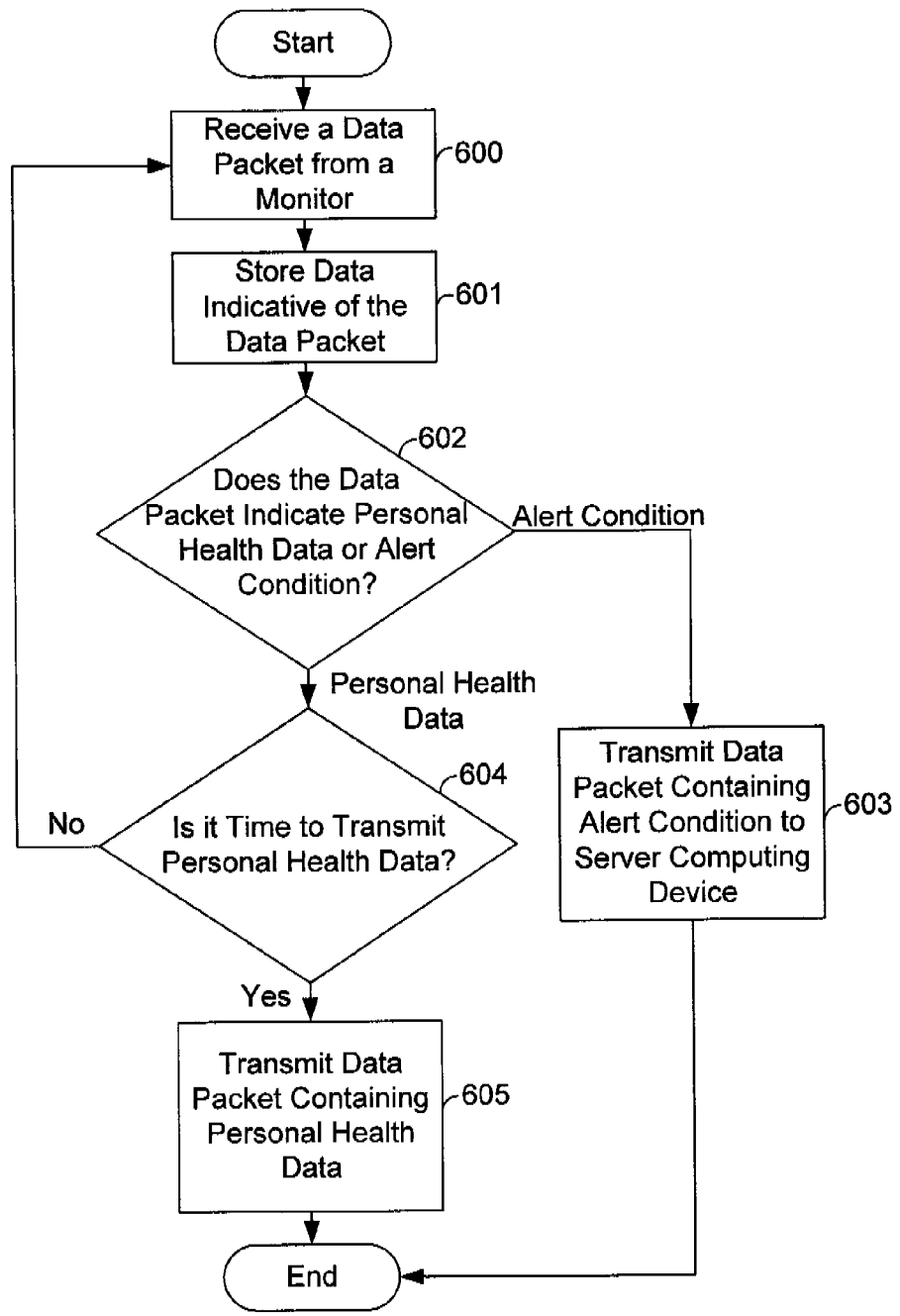
FIG. 6 is a flowchart depicting exemplary architecture and functionality of gateway controller logic of the gateway computing device depicted in FIG. 2.

FIG. 6 is a flowchart depicting exemplary architecture and functionality of the gateway controller logic 202 (FIG. 2) of the gateway computing device 109 (FIG. 2) depicted in FIG. 2. In step 600 the gateway controller logic 202 (FIG. 2) receives a data packet from a monitor 101-104 (FIG. 1). The data packet comprises unique identifiers, such as, for example, a user unique identifier and a monitor unique identifier.

In step 601 the gateway controller logic 202 stores data indicative of the data packet to memory 201 (FIG. 2). In step 602 the gateway controller logic 202 determines, based upon the contents of the data packet, whether the data packet indicates personal health data or an alert condition.

If the gateway controller logic 202 determines that the data packet indicates an alert condition in step 602, the gateway controller logic 202 transmits a data packet containing the alert condition to the server computing device 111 (FIG. 1) in step 603. If the gateway controller logic 202 determines that the data packet indicates personal health data in step 602, the gateway controller logic 202 determines if it is time to transmit personal health data to the server computing device 111. If it is time to transmit personal health data to the server computing device 111, the gateway controller logic transmits a data packet containing the personal health data to the server computing device 111 in step 605. Otherwise, the gateway controller logic 202 continues to receive data packets from monitors 101-104 in step 600.

Figure 7:
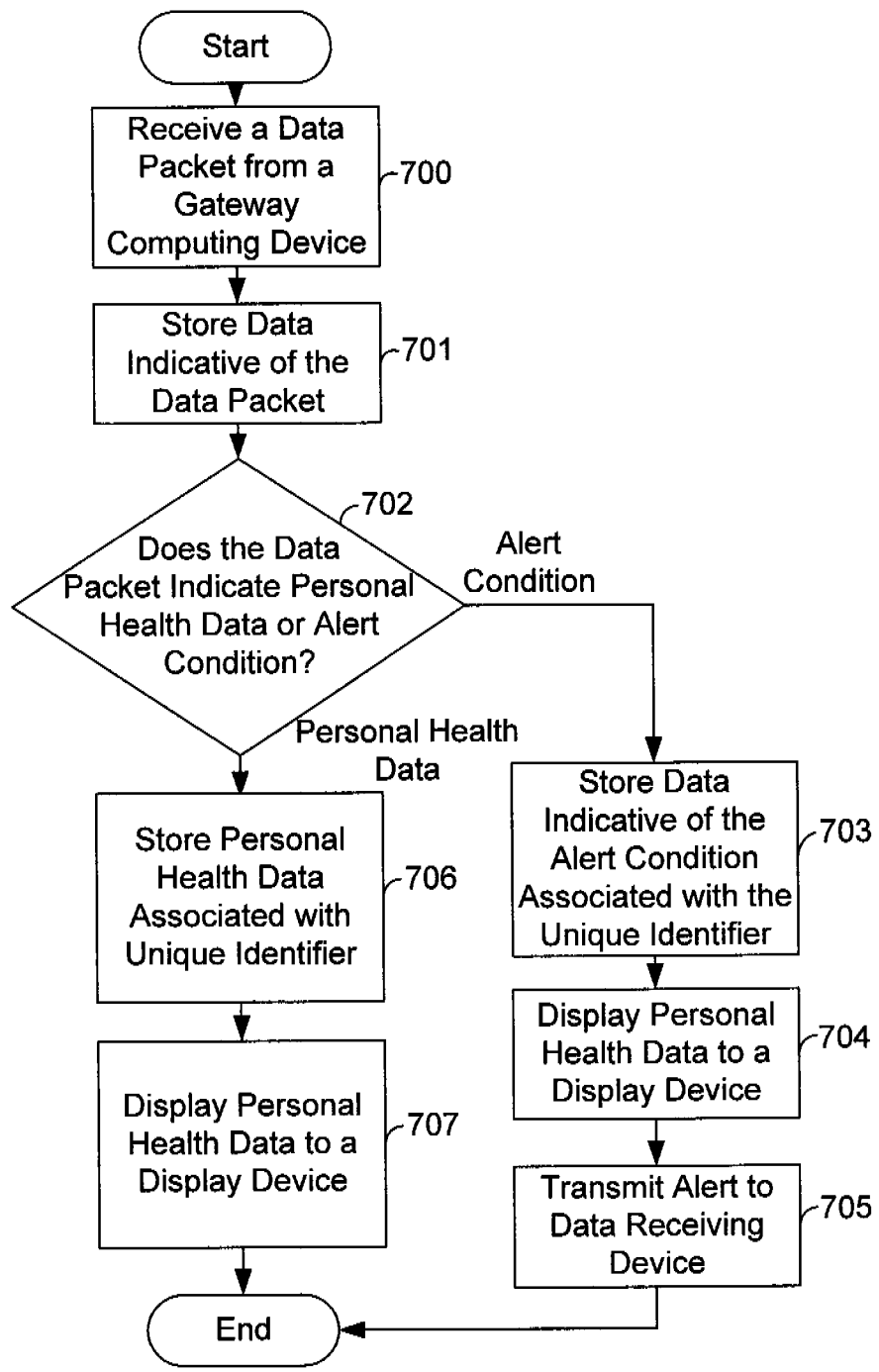
FIG. 7 is a flowchart depicting exemplary architecture and functionality of application logic of the server computing device depicted in FIG. 3.

FIG. 7 is a flowchart depicting exemplary architecture and functionality of the application logic 302 (FIG. 3) of the server computing device 111 (FIG. 3) depicted in FIG. 3. In step 700 the application logic 302 receives a data packet from the gateway computing device 109 (FIG. 1). In step 701, the application logic 302 stores data indicative of the data packet in memory 301 (FIG. 3). The data packet comprises data indicative of at least one unique identifier and personal health data or an alert condition.

In step 702 the application logic 302 determines whether the data packet indicates personal health data or an alert condition. If the application logic 302 determines that the data packet indicates an alert condition in step 702, the application logic 302 stores data indicative of the alert condition in the server database 307 (FIG. 3) associated with the unique identifier in step 703. The application logic 302 displays to the display device 305 (FIG. 3) (or to a web page via the web server 309 (FIG. 3)) data indicative of the alert condition data 209 in step 704. In step 705, the application logic 302 transmits a notification of the alert condition to a data receiving device 113 (FIG. 1).

If the application logic 302 determines that the data packet indicates personal health data in step 702, the application logic 302 stores data indicative of the personal health data associated with the unique identifier in the server database 307 in step 706. The application logic 302 then displays personal health data to a display device in step 707.

The invention claimed is:

1. A monitoring system, comprising:
   at least one wearable health monitor that collects personal health data, stores the personal health data in memory, and transmits at least one data packet comprising the personal health data and at least one identifier for identifying the monitor;
   a gateway computing device communicatively coupled to the at least one monitor and communicatively coupled to a network, the gateway computing device receives from the monitor the at least one data packet and transmits the at least one data packet over the network; and
   a server computing device communicatively coupled to the network, the server computing device receives from the gateway computing device the data packet and stores the data packet in with a user identifier, the server computing device further displays to a display device a plurality of selectable management commands and receives a selection of one or more of the selectable management commands from a user and stores the one or more selected management commands in memory corresponding to the user identifier associated with the gateway computing,
   wherein the gateway computing device periodically transmits a query to the server computing device requesting one of the selected management commands and the server computing device transmits one of the selected management commands to the gateway computing device, and in response the gateway computing device transmits an acknowledgement response after the management command is received by the gateway computing device,
   wherein the server computing device stores data associated with the transmitted management command indicating that the management command is pending, the gateway computing device executes the management command and transmits a response to the server computing device indicating that the management command was executed by the gateway computing device successfully, and the server computing device removes the management command from memory once the acknowledgement response is received from the gateway computing device.

2. The monitoring system of claim 1, wherein the gateway computing device is a cellular telephone.

3. The monitoring system of claim 1, wherein the gateway computing device is a mobile access device.

4. The monitoring system of claim 1, wherein the data packet transmitted by the monitor to the gateway computing device comprises a serial number associated with the monitor.

5. The monitoring system of claim 4, wherein the gateway computing device transmits the serial number associated with the monitor to the server computing device.

6. The monitoring system of claim 5, wherein the server computing device generates a unique user identifier and a unique monitor identifier, the unique monitor identifier based upon the serial number.

7. The monitoring system of claim 6, wherein the server computing device transmits the unique user identifier and the unique monitor identifier to the gateway computing device.

8. The monitoring system of claim 7, wherein the gateway computing device transmits the unique user identifier and the unique monitor identifier to the monitor, and the monitor stores the unique user identifier and the unique monitor identifier in memory.

9. The monitoring system of claim 8, wherein the data packet transmitted to the gateway computing device by the monitor includes the unique user identifier, the unique monitor identifier, or both.

10. The monitoring system of claim 1, wherein the gateway computing device comprises a network interface and a alternate interface.

11. The monitoring system of claim 10, wherein if the network interface is inoperable, the gateway computing device transmits data packets to the server computing device via the alternate interface.

12. The monitoring system of claim 11, wherein if the physical layer of the network interface is inoperable, the gateway computing device transmits data packets to the server computing device via the alternate interface.

13. The monitoring system of claim 12, wherein the gateway computing device periodically transmits a query to the network interface located on the gateway computing device to determine if the physical layer has become inoperable.

14. The monitoring system of claim 13, wherein if a response to the query indicates that the physical layer is operable, the gateway computing device begins to transmit data packets via the network interface.

15. The monitoring system of claim 11, wherein if the application layer of the network interface is inoperable, the gateway computing device transmits data packets to the server computing device via the alternate interface.

16. The monitoring system of claim 15, wherein the gateway computing device periodically transmits a request to the server computing device to determine if the application layer is operable.

17. The monitoring system of claim 16, wherein if a response to the request indicates that the application layer is operable, the gateway computing device begins to transmit data packets via the network interface.

18. The monitoring system of claim 10 wherein if the gateway computing device receives alert condition data, the gateway computing device simultaneously transmits the alert condition data via the network interface and the alternate interface.

19. The monitoring system of claim 1, further comprising a mobile network access device.

20. The monitoring system of claim 19, wherein the at least one wearable health monitor determines, based upon a lack of a beacon signal, that the wearable health monitor is no longer in range of the gateway computing device.

21. The monitoring system of claim 20, wherein the at least one wearable health monitor, based upon the determination that the wearable health monitor is no longer in range of the gateway computing device, transmits the at least one data packet via the mobile network access device to the server computing device.

22. The monitoring system of claim 1, wherein the gateway computing device continues to transmit queries until there are no more selected management commands corresponding to the user identifier stored in memory.

23. The monitoring system of claim 22, wherein the server computing device continues to transmit the management command to the gateway computing device if the acknowledgement response is not received by the server computing device.

24. The monitoring system of claim 23, wherein if the server computing device has transmitted the management command a threshold number of times without receiving the acknowledgement response, the server computing device no longer attempts to transmit the management command.

25. The monitoring system of claim 1, wherein the gateway computing device is communicatively coupled to a computing device for configuring the gateway computing device configuration data.

26. The monitoring system of claim 25, wherein the computing device displays a command line interface for receiving commands for modifying the configuration data.

27. The monitoring system of claim 1, wherein the gateway computing device transmits a beacon signal at particular intervals.

28. The monitoring system of claim 27, wherein the monitor receives the beacon signal and transmits a response signal to the gateway computing device.

29. The monitoring system of claim 1, wherein the wearable monitor is collects alert condition data and transmits the alert condition data to the gateway computing device.

30. The monitoring system of claim 29, wherein the gateway computing device immediately transmits a data packet comprising the alert condition data to the server computing device.

31. The monitoring system of claim 30, wherein the server computing device immediately transmits a notification indicative of the alert condition data to a data receiving device.

32. The monitoring system of claim 1, wherein the server computing device generates an alert condition that is transmitted to a data receiving device.

33. The monitoring system of claim 32, wherein the server computing device monitors data packets received from the gateway computing device and if alert condition data is detected by the server computing device, the server computing device transmits data indicative of the alert to the data receiving device.

34. The monitoring system of claim 1, wherein the server computing device invokes an operating system process that polls the memory for personal health data.

35. The monitoring system of claim 1, wherein the operating system process compares personal health data to a threshold value and if the personal health data exceeds the threshold value, the operating system process transmits data indicative of an alert condition to the data receiving device.

36. A monitoring system, comprising:
at least one wearable health monitor that collects personal health data, stores the personal health data in memory, and transmits at least one data packet comprising the personal health data and at least one identifier for identifying the monitor;
a gateway computing device communicatively coupled to the at least one monitor and communicatively coupled to a network, the gateway computing device receives from the monitor the at least one data packet and transmits the at least one data packet over the network; and
a server computing device communicatively coupled to the network, the server computing device receives from the gateway computing device the data packet and stores the data packet in memory associated with a user identifier,
wherein the gateway computing device is communicatively coupled to a computing device for configuring the gateway computing device configuration data, the computing device displays a command line interface for receiving commands for modifying the configuration data, and the command line interface is supported by reverse secure shell (SSH).

37. The monitoring system of claim 36, wherein the monitor comprises memory, and if the monitor does not receive a beacon signal, the monitor continues to collect personal health data and buffer the collected personal health data in the memory.

38. The monitoring system of claim 37, Wherein once the monitor receives the beacon signal, the monitor transmits data packets comprising the stored personal health data to the gateway computing device.

39. The monitoring system of claim 38, wherein the gateway computing device bundles the received data packets together and transmits the bundled data packets to the server computing device.

40. A monitoring method, comprising:
receiving a data packet from a wearable health monitor, the data pocket comprising at least one unique identifier and personal health data;
storing data indicative of the data packet on a gateway computing device;
repackaging the data packet;
transmitting the repackaged data packet to a server computing device, the repackaged data comprising at least one unique identifier and personal health data;
receiving the repackaged data packet;
storing data indicative of the personal health data in memory correlated with the unique identifier,
displaying to a display device a plurality of selectable management commands;
receiving a selection of one or more of the selectable management commands from a user;
storing the one or more selected management commands in memory corresponding to the user identifier associated with the gateway computing device;
periodically transmitting a query to the server computing device requesting one of the selected management commands;
transmitting one of the selected management commands to the gateway computing device;
transmitting an acknowledgement response after the management command is received by the gateway computing device;
storing data associated with the transmitted management command indicating that the management command is pending;

executing the management command on the gateway computing device;

transmitting a response to the server computing device indicating that the management command was executed by the gateway computing device successfully; and removing the management command from memory once the acknowledgement response is received from the gateway computing device.

41. The monitoring method of claim 40, further comprising transmitting queries until there are no more selected management commands corresponding to the user identifier stored in memory.

42. The monitoring method of claim 40, further comprising periodically transmitting the management command to the gateway computing device if the acknowledgement response is not received by the server computing device.

43. The monitoring method of claim 42, further comprising no longer transmitting the management command if the server computing device has transmitted the management command a threshold number of times without receiving the acknowledgement response.

44. The monitoring method of claim 40, further comprising transmitting a beacon signal at particular intervals by the gateway computing device.

45. The monitoring method of claim 44, further comprising:

receiving the beacon signal by the wearable health monitor; and transmitting a response signal to the gateway computing device.

46. The monitoring method of claim 45, wherein the monitor comprises memory, further comprising continuing to collect personal health data and buffering the collected personal health data in the memory if the monitor does not receive the beacon signal.

47. The monitoring method of claim 46, further comprising transmitting data packets comprising the stored personal health data to the gateway computing device once the monitor receives the beacon signal, the monitor transmits.

48. The monitoring method of claim 47, further comprising:

bundling the received data packets together; and transmitting the data packets to the server computing device.

49. The monitoring method of claim 40, further comprising collecting alert condition data; and transmitting the alert condition data to the gateway computing device.

50. The monitoring method of claim 49, further comprising immediately transmitting a data packet comprising the alert condition data to the server computing device.

51. The monitoring method of claim 50, further comprising immediately transmitting a notification indicative of the alert condition data to a data receiving device.

52. The monitoring method of claim 40, further comprising:

generating, by the server computing device, an alert condition; and transmitting data indicative of the alert condition to a data receiving device.

53. The monitoring method of claim 52, further comprising:

monitoring data packets received from the gateway computing device; and if alert condition data is detected by the server computing device, transmitting data indicative of the alert to the data receiving device.

54. The monitoring method of claim 40, further comprising invoking an operating system process that polls memory for personal health data.

55. The monitoring method of claim 54, further comprising:

comparing personal health data to a threshold value by the operating system process; and if the personal health data exceeds the threshold value, transmitting data indicative of an alert condition to the data receiving device by the operating system process.

56. A monitoring method, comprising:

receiving a data packed from a wearable health monitor, the data packet comprising at least one unique identifier and personal health data;

storing data indicative of the data packet on a gateway computing device;

repackaging the data packet;

transmitting the repackaged data packet to a server computing device, the repackaged data comprising at least one unique identifier and personal health data;

receiving the repackaged data packet;

storing data indicative of the personal health data in memory correlated with the unique identifier;

configuring the gateway computing device configuration data via computing device coupled to the gateway computing device; and displaying a command line interface for receiving commands for modifying the configuration data, wherein the command line interface is supported by reverse secure shell (SSH).

* * * * *